(12) United States Patent
Ermer et al.

(10) Patent No.: US 7,084,283 B2
(45) Date of Patent: Aug. 1, 2006

(54) SYNTHESIS OF FLUORINATED MOLECULES POSSESING HIGH OPTICAL NON-LINEARITY

(75) Inventors: Susan Ermer, Redwood City, CA (US); Steven Michael Lovejoy, Sunnyvale, CA (US); Peter V. Bedworth, Palo Alto, CA (US)

(73) Assignee: Lockheed Martin Corporation, Bethesda, MD (US)

( * ) Notice: Subject to any disclaimer, the term of this patent is extended or adjusted under 35 U.S.C. 154(b) by 285 days.

(21) Appl. No.: 10/473,478

(22) PCT Filed: Mar. 27, 2002

(86) PCT No.: PCT/US02/09324

§ 371 (c)(1),
(2), (4) Date: Apr. 16, 2004

(87) PCT Pub. No.: WO02/076969

PCT Pub. Date: Oct. 3, 2002

(65) Prior Publication Data

US 2004/0158084 A1    Aug. 12, 2004

Related U.S. Application Data

(60) Provisional application No. 60/278,762, filed on Mar. 27, 2001.

(51) Int. Cl.
   *C07D 307/30*    (2006.01)
(52) U.S. Cl. ...................................................... 549/474
(58) Field of Classification Search .................. 549/474
   See application file for complete search history.

(56) References Cited

U.S. PATENT DOCUMENTS

| 6,067,186 A | 5/2000 | Dalton et al. |
| 6,348,992 B1 | 2/2002 | Zhang et al. |
| 6,361,717 B1 | 3/2002 | Dalton et al. |
| 6,555,027 B1 | 4/2003 | Wang et al. |

FOREIGN PATENT DOCUMENTS

| WO | WO 00 09613 A | 2/2000 |
| WO | WO 01/79750 A1 | 10/2001 |

OTHER PUBLICATIONS

Kirk-Othmer Encyclopedia of Chemical Technology, 4th Edition, vol. 17 (John Wiley & Sons, New York, 1995), pp. 288-302.
Liakatas et al., Importance of Intermolecular Interactions in the Nonlinear Optical Properties of Poled Polymers, Applied Physics Letters, American Institute of Physics, New York, US, vol. 76, No. 11, Mar. 13, 2000), pp. 1368-1370.

*Primary Examiner*—Taofiq Solola
(74) *Attorney, Agent, or Firm*—McDermott Will & Emery LLP

(57) ABSTRACT

A compound of formula (I) wherein R', R'', R''', R'''', R''''' can be selected from the group consisting of alkyl, aryl, a heteroatom, substituted alkyl and substituted aryl groups for use as a chromophore in electro-optic devices.

1 Claim, No Drawings

SYNTHESIS OF FLUORINATED MOLECULES POSSESING HIGH OPTICAL NON-LINEARITY

This application is based on Provisional Application 60/278,762 filed Mar. 27, 2001.

FIELD OF THE INVENTION

The present invention relates to novel organic chromophores and methods of making and using the same.

BACKGROUND OF THE INVENTION

Known materials for use in electro-optic devices include both organic and inorganic materials. Semiconductor materials such as gallium arsenide, organic crystalline materials and organic materials prepared by sequential synthesis methods are used as well as electrically poled polymer films containing organic chromophores incorporated either physically to form composites or chemically to form homopolymer materials. See Kirk-Othmer Encyclopedia of Chemical Technology, $4^{th}$ Edition, Volume 17 (John Wiley & Sons, New York, 1995) pp. 288–302.

When an electric field is applied to electro-optic materials, the highly polarizable electrons in those materials change significantly resulting in an increase in the index of refraction of the materials and a decrease in the speed of light passing through the materials. The change in the index of refraction can be used to impose electric signals onto optical signals to switch optical signals in a network or to control a beam of light.

The most commonly used inorganic material is lithium niobate which possesses an electro-optic coefficient on the of 35 pm/V which results in a typical drive voltage of about 5 volts. Because lithium niobate has a high dielectric constant which results in velocity mismatch of electric and optical waves propagating in the material, a short interaction length and limiting bandwidth results. In one analysis a one centimeter electro-optic modulator constructed from lithium niobate typically has a bandwidth of less the 10 Gigahertz.

In using organic materials systems, one obstacle to overcome is the decay of the poled electro-optic response at the elevated manufacturing and operating temperatures dictated by current electronic technology.

For generally useful devices, higher temperature electro-optic thermal stability is required. In some manufacturing processes, short-term temperature excursions can be high than 300 degrees C. In fabrication, the poling and curing temperatures of an electro-optic polymer for integrated devices may often exceed this limit.

SUMMARY OF THE INVENTION

Accordingly, It is an object of the present invention to provide an electro-optic material that does not suffer from the limitations of prior materials used in the art.

It is a further object to provide a new class of highly hyperpolarizability organic chromophors.

It is yet a further object of this invention to show a process for synthesizing the novel highly hyperpolarizable organic chromphores.

Another object is to provide devices such as electro-optical modulators employing the new class of novel highly hyperpolarizable organic chromphores.

These and other objects of the present invention will become clear from the detailed description of the invention and the claims included below.

DETAILED DESCRIPTION OF THE INVENTION

It is the purpose of this invention to make a nonlinear optical material in a polymer host. The functional material is a nonlinear optical material. It is made up of a polymer and a nonlinear optical dye or chromophore.

Nonlinear optical chromophores or dyes are constructed from three segments which include a donor material, a pi-conjugated bridge, and an acceptor. The donor is electron rich when compared to the acceptor and the bridge allows communication between the donor and the acceptor. To optimize the molecular hyperpolarizability or beta, one must strike a balance between the electron donating of the donor side and the electron accepting ability of the acceptor side such that the hyperpolarizability is optimized.

The current state of art chromophores have not been optimized for beta. The present invention chemically modifies a well studied acceptor to give rise to a more potent acceptor that does optimize the beta values in these chromophores. It does, however, not increase the ground state dipole or mu as expected. In addition it optimizing the beta values.

The following describes the chromophore or dye of this invention.

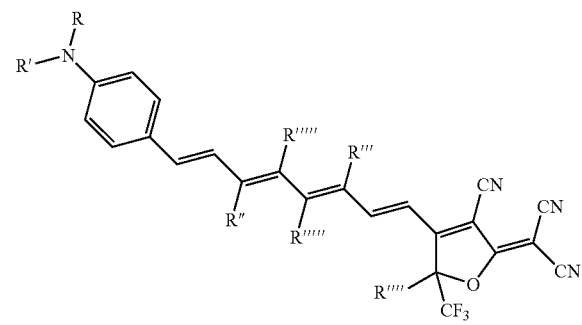

Where R', R", R"', R"", R""" can be selected from the group consisting of alkyl. aryl, a heteroatom, substituted alkyl and substituted aryl groups.

The following is the aldehyde may be used in this invention.

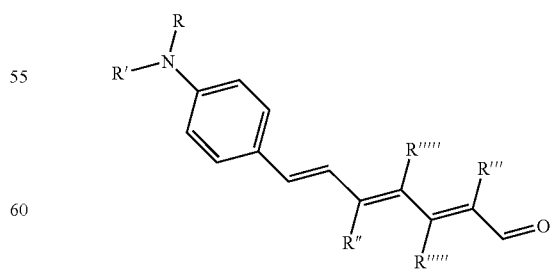

Where R', R", R"', R"", R""" can be selected from the group consisting of alkyl. aryl, a heteroatom, substituted alkyl and substituted aryl groups.

The following is the acceptor which can be employed in this invention.

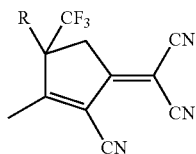

Where R can be selected from the group consisting of alkyl. aryl, a heteroatom, substituted alkyl and substituted aryl groups.

The reaction here is the Knovenegal condensation and is accomplished by putting the reactants together in solvents. While catalysts which are conventionally used in the art can be employed, in many cases no catalyst is required.

A preferred product in this invention is 2-[4-(3-{3-[2-(4-{Bis-[2-(tert-butyl -dimethyl-silanyloxy)-ethyl]-amino}-phenyl)-vinyl]-5,5-dimethyl-cyclohex-2-enylidene}-propenyl)-3-cyano-5-methyl-5-trifluoromethyl-5H-furan-2-ylidene]-malononitrile. This is made from {3-[2-(4-{Bis-[2-(tert-butyl-dimethyl-silanyloxy)-ethyl]-amino}-phenyl)-vinyl]-5,5-dimethyl-cyclohex-2-enylidene}-acetaldehyde which is reacted with 2-(3-Cyano-4,5-dimethyl-5-trifluoromethyl-5H-furan-2-ylidene)-malononitrile.

To make this preferred product, the malononitrile acceptor is made by reacting 4,4,4-Trifluoro-3-hydroxy-3-methyl-butan-2-one with 2 equivalents of malonitrile in the presence of a lithium hydroxide catalyst.

The doner material is described in the literature and its preparation is well known to those of ordinary skill in the art.

By following the above, the chromophore of this invention can be poled at lower field and has increased temporal stability. Temporal stability occurs when the nonlinear optical properties are maintained over time. This is a result of a reduction in electrostatic interaction between dye molecules.

What is claimed is:

1.

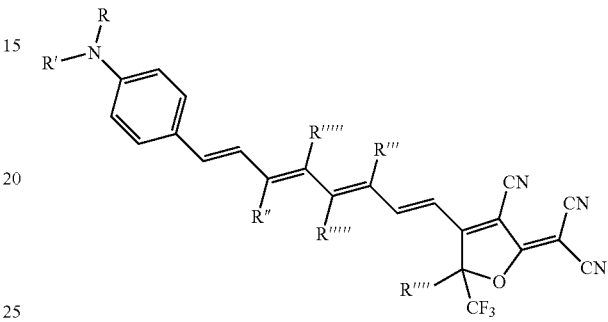

where R', R'', R''', R'''' can be selected from the group consisting of alkyl aryl, a heteroatom, substituted alkyl and substituted aryl groups.

* * * * *

UNITED STATES PATENT AND TRADEMARK OFFICE
CERTIFICATE OF CORRECTION

PATENT NO.         : 7,084,283 B2
APPLICATION NO. : 10/473478
DATED                  : August 1, 2006
INVENTOR(S)        : Susan P. Ermer et al.

It is certified that error appears in the above-identified patent and that said Letters Patent is hereby corrected as shown below:

ON THE TITLE PAGE:

(54) Title: "SYNTHESIS OF FLUORINATED MOLECULES POSSESING HIGH OPTICAL NON-LINEARITY", should read: -- SYNTHESIS OF FLUORINATED MOLECULES POSSESSING HIGH OPTICAL NON-LINEARITY--

IN THE SPECIFICATION:

Column 3, lines 5-10, please replace the acceptor diagram with:

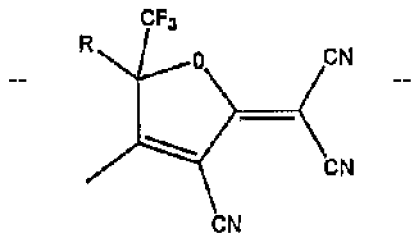

Column 4, line 10, please add the following paragraphs:

--The chromophore of this invention shows improvement over the previous dyes because of the presence of the trifluoromethyl group on the acceptor portion of the molecule. This was a surprise because inductively withdrawing substituents on an acceptor was not expected to increase acceptor strength.

Useful products from the materials this invention maybe composed of polymers, such as, for example polyquinolines, polycarbonates, polyesters, polyurethanes, and other similar materials. The polymers should have a glass transition temperature or Tg which is sufficiently high so that the chromophore will be locked into place after poling but not so high that the chromophore decomposes. The polymer should be transparent at the useful wavelength. A particularly useful polymer is amorphous polycarbonate.--

UNITED STATES PATENT AND TRADEMARK OFFICE
CERTIFICATE OF CORRECTION

PATENT NO. : 7,084,283 B2
APPLICATION NO. : 10/473478
DATED : August 1, 2006
INVENTOR(S) : Susan P. Ermer et al.

It is certified that error appears in the above-identified patent and that said Letters Patent is hereby corrected as shown below:

Column 4, line 27, Replace: "R', R", R''', R'''',"
with --R', R'', R''', R'''', R'''''--

Signed and Sealed this

Sixth Day of November, 2007

JON W. DUDAS
*Director of the United States Patent and Trademark Office*